United States Patent [19]
Crawford et al.

[11] 4,179,757
[45] Dec. 25, 1979

[54] BIOCOMPATIBLE ARTICLES HAVING HIGH PERMEABILITY TO GASES DERIVED FROM POLYSULFONES

[75] Inventors: James E. Crawford, Adrian, Mich.; Don N. Gray, Sylvania, Ohio

[73] Assignee: Owens-Illinois, Inc., Toledo, Ohio

[21] Appl. No.: 684,683

[22] Filed: May 10, 1976

Related U.S. Application Data

[60] Continuation of Ser. No. 577,533, May 14, 1975, abandoned, which is a division of Ser. No. 328,972, Feb. 2, 1973, Pat. No. 3,928,294, which is a continuation-in-part of Ser. No. 279,877, Aug. 11, 1972, abandoned, which is a continuation-in-part of Ser. No. 228,240, Feb. 22, 1972, abandoned.

[51] Int. Cl.² .......................... A61F 1/24; A61F 1/22; C08G 75/22
[52] U.S. Cl. .............................................. 3/1; 3/1.4; 3/1.5; 3/1.7; 128/156; 128/348; 351/160 R; 528/385; 528/386
[58] Field of Search ................ 3/1, 1.4, 1.5; 128/156, 128/348; 210/500 M; 351/160

[56] References Cited

U.S. PATENT DOCUMENTS

| | | | |
|---|---|---|---|
| 2,190,836 | 2/1940 | Harmon | 260/79.3 A |
| 2,201,544 | 5/1940 | Marvel | 260/79.3 A |
| 2,972,779 | 2/1961 | Cowley | 3/1.4 |
| 3,563,789 | 2/1971 | Moore | 260/79.3 A |
| 3,579,642 | 5/1971 | Heffernan | 3/1 |
| 3,640,269 | 2/1972 | Delgado | 128/2 R |
| 3,651,030 | 3/1972 | Desaulniers | 260/79.3 |
| 3,728,185 | 4/1973 | Gray | 156/89 |
| 3,765,414 | 10/1973 | Arlen | 128/260 |
| 3,792,026 | 2/1974 | Atkins | 260/79.3 A |
| 3,798,185 | 3/1974 | Skiens | 260/2.5 M |
| 3,810,468 | 5/1974 | Harper | 128/156 |
| 3,852,388 | 12/1974 | Kimura | 264/41 |
| 3,941,858 | 3/1976 | Shepherd | 260/885 |

Primary Examiner—C. A. Henderson
Attorney, Agent, or Firm—John R. Nelson; Myron E. Click; David H. Wilson

[57] ABSTRACT

There is disclosed the preparation of an alpha-olefin-sulfur dioxide copolymer derived from the $C_8$ to $C_{18}$ alpha-olefins. The polymers undergo clean thermal degradation, having high permeabilities to oxygen and carbon dioxide, and are readily processed into a membrane article. Maximum permeabilities are obtained with the $C_{16}$ based polymer. New uses of the copolymer are set forth including perfusion membranes, soft contact lenses and biocompatible articles for contact with human body fluids including surgical tubing, wound dressings, and prosthetic devices such as artificial veins, arteries and heart valves.

11 Claims, 12 Drawing Figures

5 — SOFT CONTACT LENS

MEMBRANE-LINED CAPILLARY OXYGENATOR

8 — SURGICAL TUBING

BIOCOMPATIBLE ARTICLES HAVING HIGH PERMEABILITY TO GASES DERIVED FROM POLYSULFONES

RELATED APPLICATIONS

This is a continuation application of copending U.S. patent application Ser. No. 577,533, filed May 14, 1975 now abandoned which, in turn, is a divisional application of U.S. patent application Ser. No. 328,972 filed Feb. 2, 1973 and now issued as U.S. Pat. No. 3,928,294 which, in turn, is a continuation-in-part of U.S. patent application Ser. No. 279,877 filed Aug. 11, 1972 and now abandoned which, in turn, is a continuation-in-part of U.S. patent application Ser. No. 228,240, filed Feb. 22, 1972 and now abandoned.

This invention relates to the preparation of polymeric materials which undergo clean thermal degradation, have increased permeabilities, and are readily processable. More particularly, this invention relates to the preparation of a novel permselective membrane article consisting of an alpha-olefin-sulfur dioxide copolymer and having high biocompatibility and high permeability to gases, especially oxygen and carbon dioxide.

Copolymers from simple olefins and $SO_2$ have been known for some time. They were first reported by Matthews and Elder in British Pat. No. 11,635 in 1915, although the material prepared was not identified as being polymeric. Seyers and King, J. Amer. Chem. Soc. 55, 3140, in 1933 were the first to accurately describe an olefin heteropolymer of sulfur dioxide. Characterization of these compounds as high molecular weight materials was accomplished independently by Marvel and Staudinger. Reference is made to J. Amer. Chem. Soc., 56, 1915 (1934); J. Amer. Chem. Soc., 57, 1691 (1935); and Ber Bunsenges. Phys. Chem., 68,455 (1935). Both recognized that an AB-type copolymer was obtained regardless of monomer concentration, and they correctly deduced that the active polymerizing species was an olefin-sulfur dioxide complex. Marvel and Weil later showed the polysulfone structure to be a head-to-tail configuration as evidenced from the preparation of various reference compounds that were compared with the hydrolysis products of the polymers. See J. Amer. Chem. Soc., 76, 61 (1954).

Marvel characterized a number of olefin-sulfur dioxide polymers using pyrolysis techniques. Naylor and Anderson, J. Amer. Chem. Soc., 76, 3962 (1954), prepared copolymers of ethylene, propylene, 2-butene, and isobutylene with $SO_2$ at 65°–70° C. using radical catalysts. They found that the propylene-sulfur dioxide polymer started to degrade at about 180° C. with an activation energy of 32 kcal/mole determined from data obtained between 180° and 260° C. ($T_c$ for this polymer is 62.5° C.). Pyrolysis of the propylene-based polymer in nitrogen at 280°–290° C. yielded 95.4% volatile products, with 83.4% of the initial polymer weight being monomers. Water and some unidentified sulfur-containing compounds were also isolated.

This invention is related to the preparation and properties of poly(alpha-olefin sulfones) prepared from the Series $C_8$–$C_{18}$ alpha-olefins and sulfur dioxide and the use of such polymers is a permselective membrane.

Polymeric membranes having gaseous permeability are known in the prior art. Typically such membranes have comprised silicones or modified silicones. However, the processing of such silicones is difficult. Likewise, pure polysilicone materials tend to have poor mechanical properties and may require the use of silica or other fillers. Such fillers may compromise the ultimate performance of the polysilicone as a blood compatible bio-material.

In accordance with this invention, there is provided a polymeric material having gaseous permeability, biocompatibility, and suitable mechanical properties and which can be readily processed into a membrane article.

More especially, in accordance with this invention there is provided a novel membrane article of manufacture having high permeability, excellent non-thromobogenic properties to blood, and improved mechanical properties and consisting of a poly(alpha-olefin-sulfone) prepared from the series $C_8$ to $C_{18}$ alpha-olefins and sulfur dioxide, said poly(alpha-olefin-sulfone) having the chemical structure:

where R is a straight chained, branched, or cyclic alkyl hydrocarbon radical containing six (6) to sixteen (16) carbon atoms.

The polymer is typically prepared via the reaction:

where [o] is any suitable catalyst such as a free radical source, light, peroxide, or azo nitrile and where R is a straight chained, branched or cyclic alkyl hydrocarbon group of six (6) to sixteen (16) carbons.

It is contemplated reacting a mixture of alpha-olefins with the $SO_2$. Typically the $SO_2$ and the alpha-olefin(s) are reacted in a molar ratio of 1:1.

The following represents certain experimental results and some of the best embodiments contemplated by the inventors in the practice of this invention.

Monomer Purity

Commercial alpha olefins having a minimum mono-olefin content of 98.5% (remainder being normal paraffins) were used in this study. Gas-chromatographic analysis showed less than 2% olefinic impurities consisting of other alpha-olefins.

Polymerization

Bulk polymerization was used to prepare the series based on the $C_6$–$C_{18}$ even numbered alpha-olefins and sulfur dioxide. A clean, dry nitrogen-purged citrate bottle was cooled in an ice water bath, then liquified sulfur dioxide was added. The olefin containing 1% tert-butyl hydroperoxide, based on the olefin, was then added slowly to the citrate bottle. With an addition of a small amount of the olefin, approximately one-fourth of the total quantity, a rapid reaction occurred, resulting in a loss of some $SO_2$. After the remaining olefin-peroxide mixture was added, the bottle was capped with a lined, ventable cap and the contents were allowed to warm to room temperature. Following a predetermined reaction period, usually 20 hr. at room temperature, the bottle was vented and the contents were removed. The product was kept at reduced pressure to remove the residual monomers.

Molecular Weights

Molecular weight ($M_n$) (membrane osmometer) were all above 100,000, and some were as high as 350,000.

Differential Thermal Analysis

Figure 1:
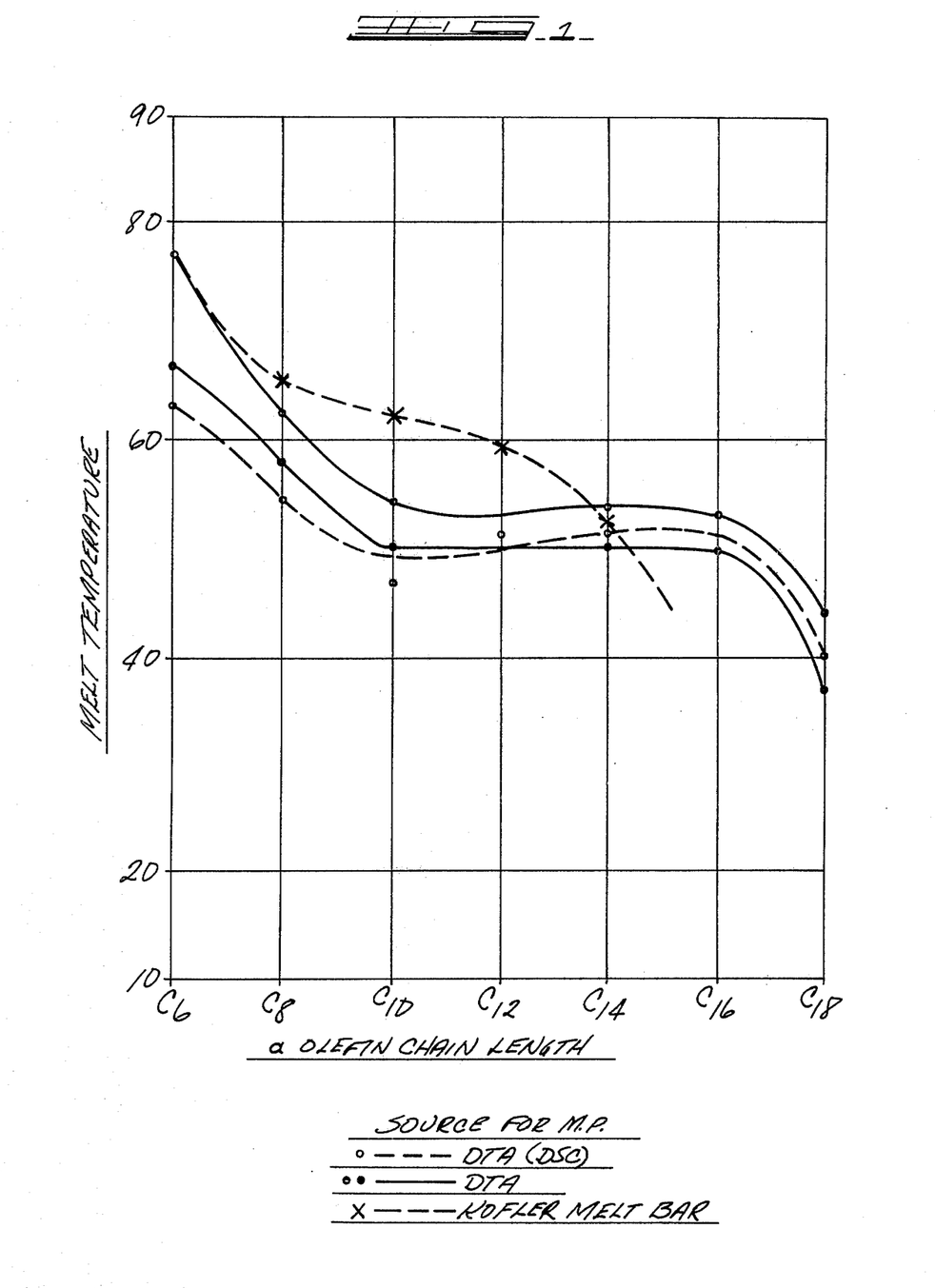

Polymer melt temperatures were obtained using the standard capillary (micro) cell of the duPont 900 instrument, the duPont 900 with the DSC cell module, and visually using a Kofler melt bar. These data are shown in FIG. 1. All melt data were obtained on polymers having molecular weight ($M_n$) in excess of 150,000. It was not possible to obtain accurate glass transitions since several other second-order transformations appeared to be occurring in the temperature region where one would expect the $T_g$ to occur.

Thermogravimetric Analysis

Thermogravimetric analysis (TGA) was obtained on a duPont 900 unit in both air and nitrogen atmospheres. For screening purposes for a particular polymerization run, a heating rate of 20° C./min in air with a sample size of about 10–15 mg was used. Generally the polymer decomposed cleanly. Pyrolysis started at 175° C. and was essentially complete when the temperature reached 275° C. One $C_{14}$ polymer sample ($M_n$ 136,000) was used to obtain kinetic data (pyrolysis) using the method of Wall and Flynn, Polymers Letters, 4, 323 (1966). TGA data were obtained as heating rates of 5°, 10°, 15° and 20° C./min in air. The average activation energy for the pyrolytic decomposition was found to be 46–47 kcal/mole.

Mass-Spectrometric Thermal Analysis and Pyrolysis Gas-Chromatrographic Analysis Mass-spectrometric thermal analysis was accomplished using the solid sample wand of the Varian M-66 mass spectrometer. The sample used was the $C_{14}$ polymer used for the kinetic TGA runs. A wand temperature of 250° C. yielded mass spectra differing only from the fragmentation pattern of the pure $C_{14}$-alpha-olefin by peaks at 64 and 48 mass units corresponding to the $SO_2$ and SO ion species.

For higher temperature pyrolysis studies, pyrolysis gas chromatography was utilized. A Perkin-Elmer pyrolyzer was connected to a gas chromatograph equipped with a hydrogen flame detector and a 20% carbowax/firebrik column. Separate samples of the $C_{14}$ copolymer were heated rapidly to 400°, 600°, and 800° C. in the pyrolysis chamber. At 400° C., only the $C_{14}$-alpha-olefin was detected. At 600° C., about equal amounts of the olefin and lighter pyrolysis products were found, while at 800° C., only complete pyrolysis products consisting of methane, ethylene, ethane, propylene, and propane were found.

Density

Figure 2:
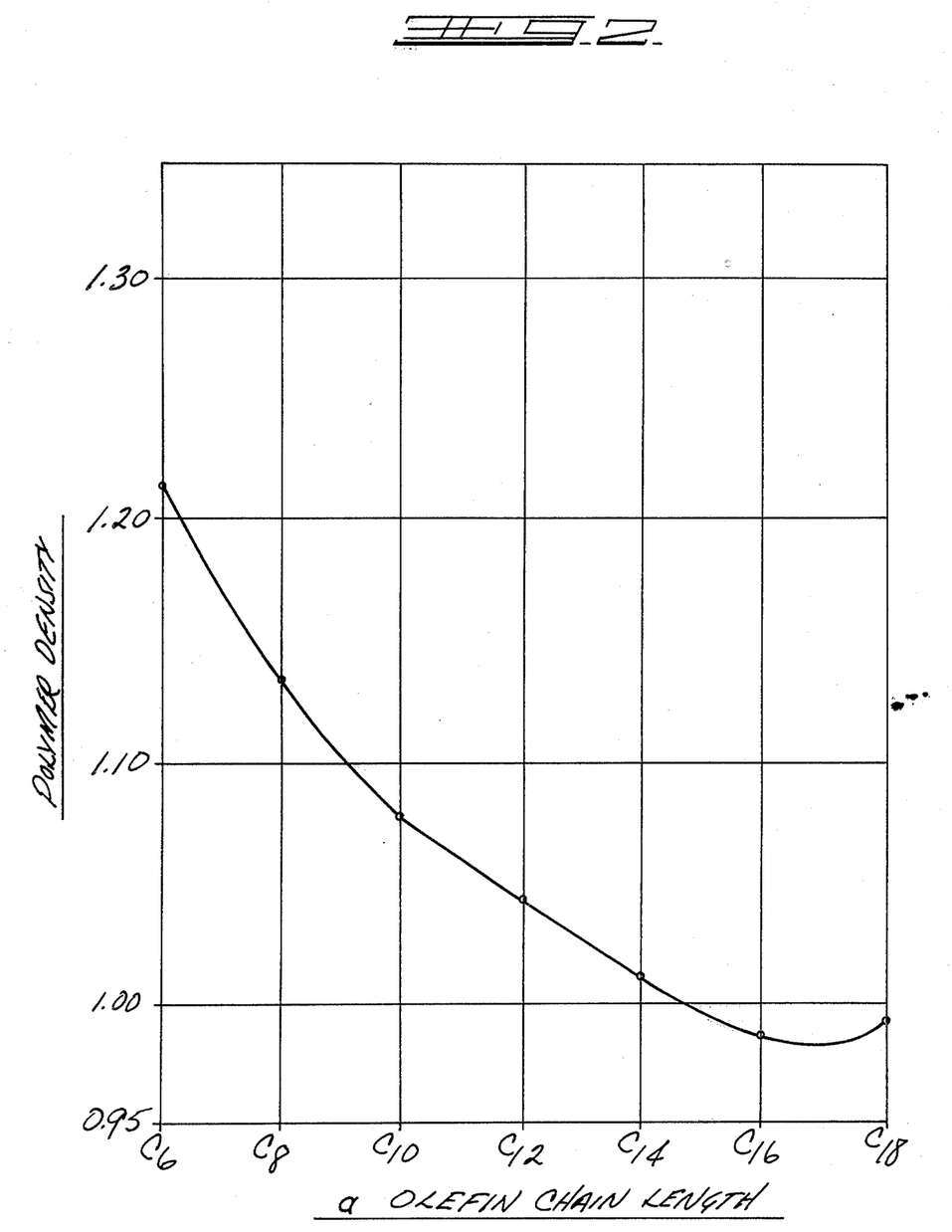
FIG. 2 plots the alpha-olefin chain lengths from $C_6$ to $C_{18}$ carbon atoms against polymer density.

Density as a function of chain length was determined on the polymer series using a density gradient column. These data are shown in FIG. 2.

Permeability

Figure 3:
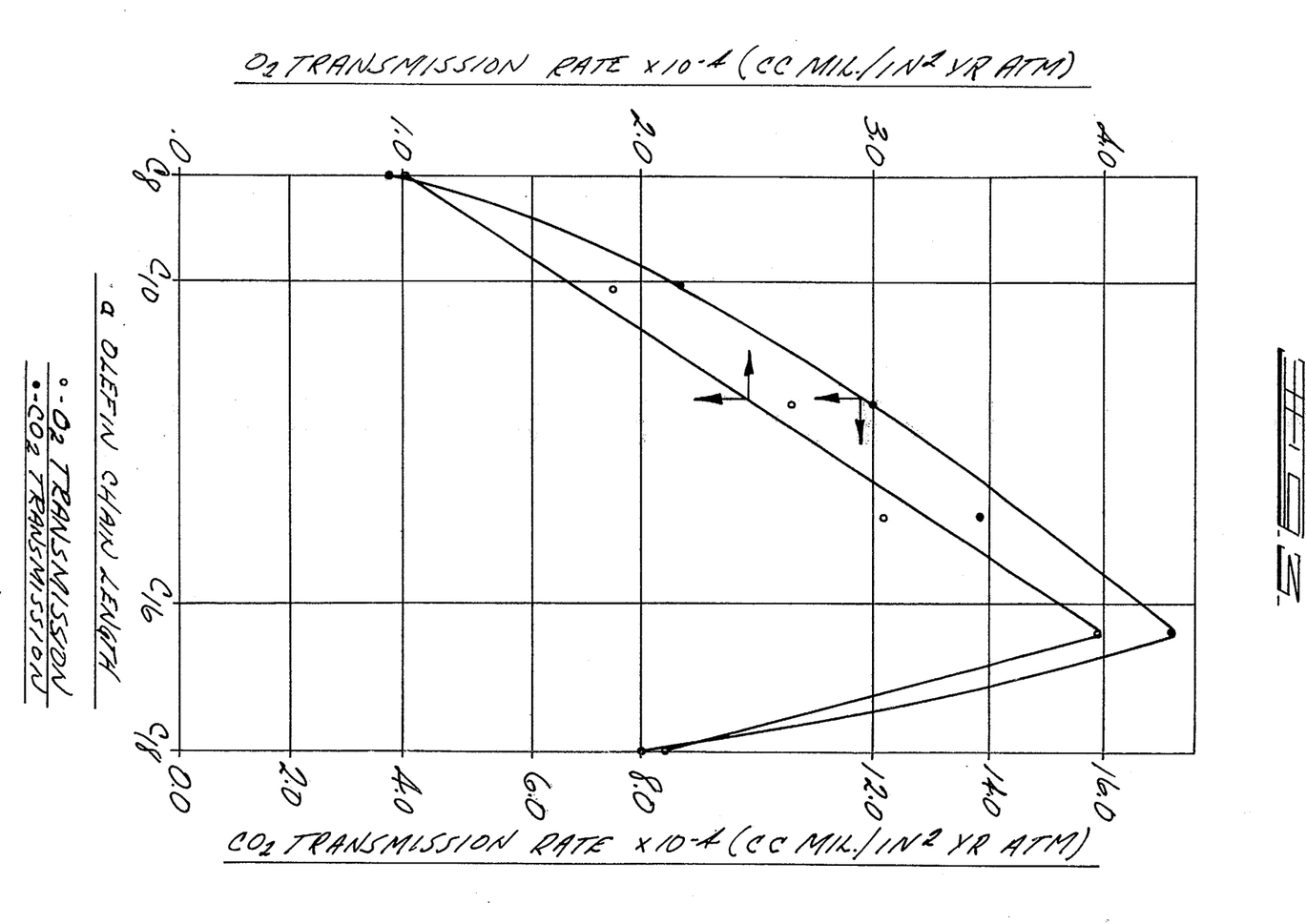
FIG. 3 indicates the relationship between the olefin chain length and the $O_2$ transmission rate as well as the $CO_2$ transmission rate, each of the respective transmission rates being plotted against the alpha-olefin chain length from $C_8$ to $C_{18}$ carbon atoms.

The gaseous permeability to oxygen and carbon dioxide of this series of polymers is quite high, with only the silicones and modified silicones showing high permeability. The relationship between alpha-olefin chain length and gaseous permeability (oxygen and carbon dioxide) for the $C_8$–$C_{18}$ series is plotted in FIG. 3. Permeability was determined by a modified Linde volumetric cell on films from polymers having molecular weight in excess of 150,000 ($M_n$).

Tensile Modulus and Elongation

Figure 4:
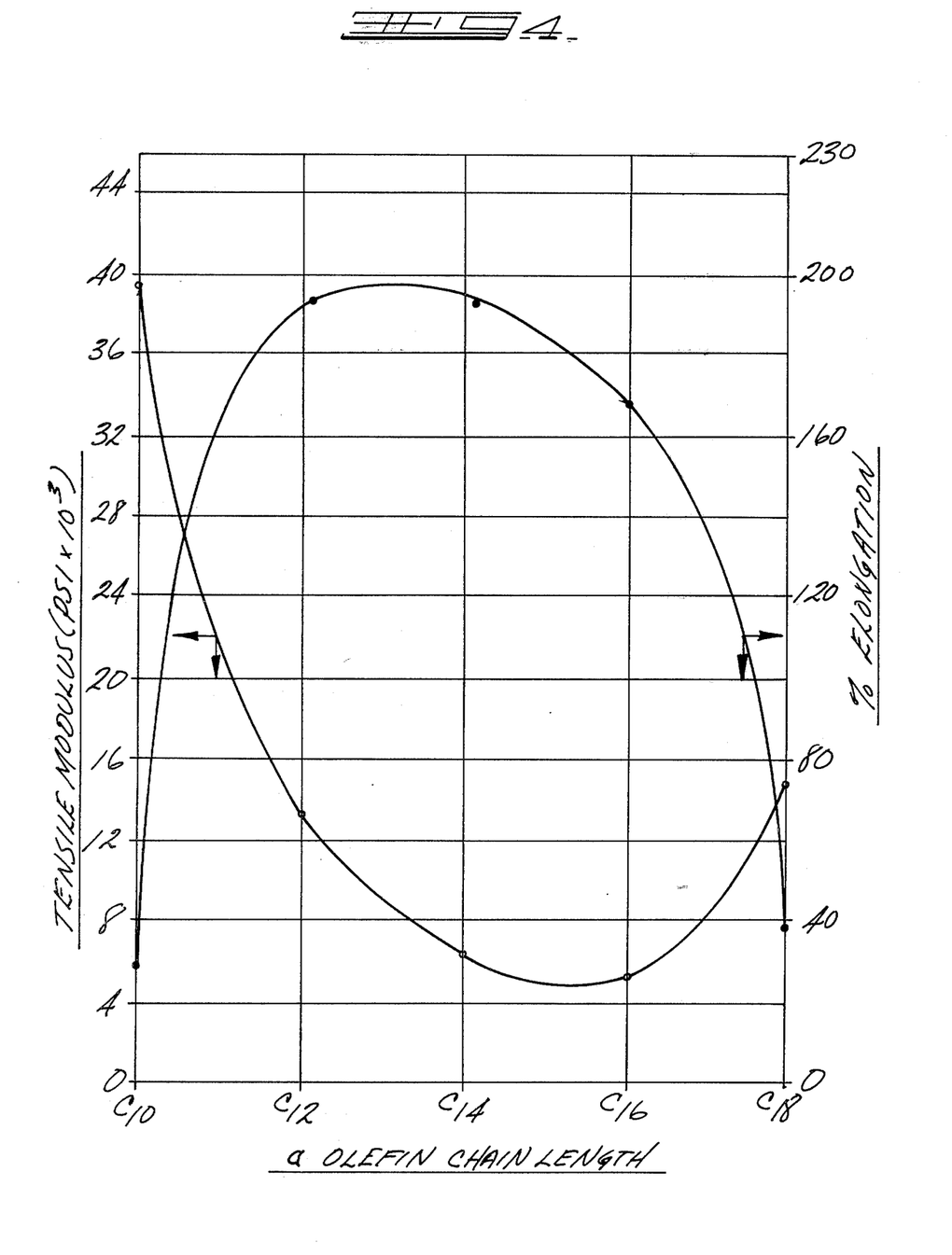
FIG. 4 plots the alpha-olefin chain length against tensile modulus and percent elongation.
Figure 5:
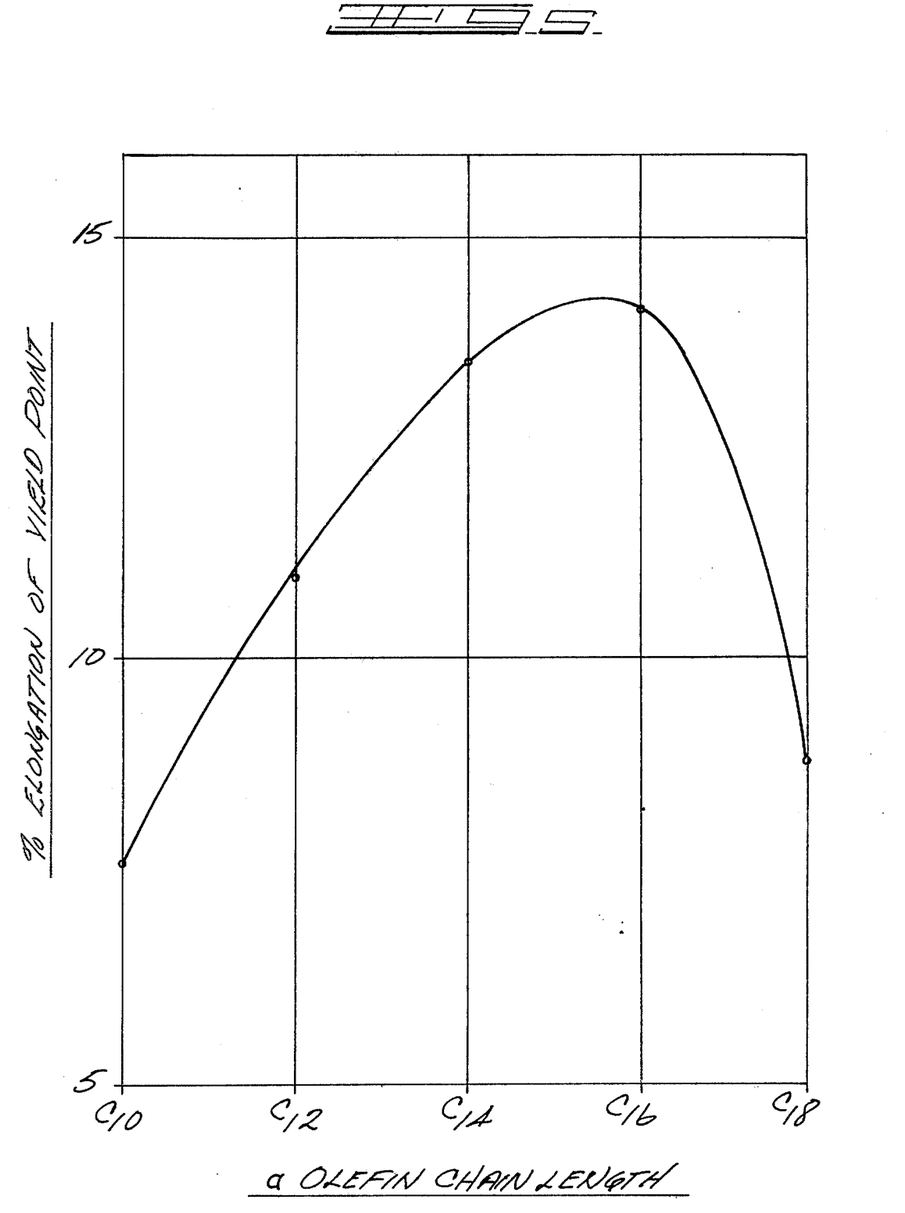
FIG. 5 plots the alpha-olefin chain length against the percent elongation at yield point.
Figure 6:
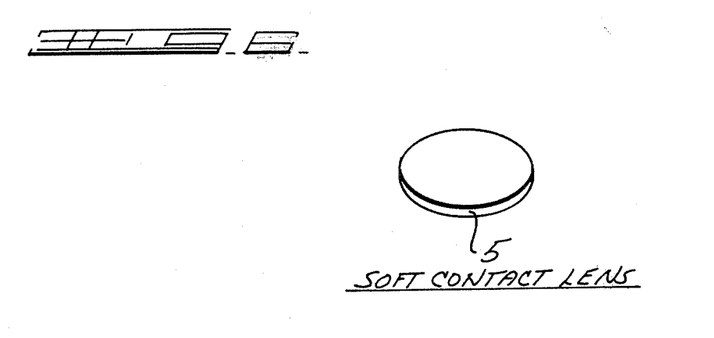

Samples of polymers from the same polymerization run as those submitted for permeability studies were used to determine the mechanical properties (tensile modulus, percent elongation, and ultimate elongation). These are presented in FIGS. 4 and 5.

Data were obtained in accordance with ASTM Method No. 1708 with a cross-head speed of 0.5 in./min, the gauge length 0.90 in., a chart speed of 20 in./min, 74° F., and a relative humidity of 53%.

RESULTS AND DISCUSSION

It has been recognized that the olefin-$SO_2$ copolymers are not thermally stable and that thermal degradation occurs via an unzipping mechanism to yield mostly monomers. Mass-spectrometric thermal analysis indicates that the original comonomers are the only products of vacuum-pyrolytic degradation, and no other sulfur-containing products were found such as described by Naylor and Anderson; J. Amer. Chem. Soc., 76, 3962 (1954).

At higher temperatures under essentially flash pyrolysis conditions, the decomposition mechanism appears to be a chain-unzipping one to form the alpha-olefin and sulfur dioxide, followed by the pyrolysis of the alpha-olefin. An activation energy for degradation of approximately 46 kcal/mole is in line with a similar activation energy for pyrolysis of other chain-unzipping polymers such as polystyrene, variously reported from 55 to 70 kcal/mole, and poly(methyl methacrylate), a good average being 40 kcal/mole. Initiation of degradation is in the 175° C. range, and pyrolysis is generally complete at 225° C. with a heating rate of 20° C./min. It is noted that this value given for the activation energy is for the pyrolysis of the molten polymer, since the polymer melt temperatures for all of the polymers were well below their 175° C. decomposition points. There is no real difference in the pyrolysis characteristics of the polymers as a function of chain length of the alpha-olefin comonomer. This is not unexpected since the rate-determining step must involve an endgroup initiation or a chain scission of a carbon-sulfur linkage. The alpha-olefin tail could be expected to play no great part in guiding the course of the pyrolytic reaction.

Variation of Properties of Function of Chain Length

In the series studied, the polysulfones prepared from the commercial olefins range from a hard, brittle material prepared from the $C_6$-alpha-olefin to an elastomer obtained from the $C_{16}$-olefin. It can be seen from FIG. 5 that the permeabilities of oxygen and carbon dioxide reach a maximum at the $C_{16}$-based polymer. Also the tensile and elongation curves show a break at the $C_{16}$-polymer. In addition, the minimum density is obtained with the $C_{16}$-based polymer as shown in FIG. 2. Our explanation for this behavior is that a plasticizing effect with the longer alpha-olefin chain is occurring since it can be shown that a $C_{16}$ alpha-olefin can flexibilize a $C_6$-alpha-olefin-sulfone polymer. The plasticizing effect should become more efficient as the chain length of the alpha-olefin increases. However, we believe another effect occurs at $C_{18}$, specifically, side chain crystallization. In this case the olefin side chain crystallizes independently of the backbone of the polymer, thus lowering its mobility and its plasticizing action on the main chain of the polymer. Side chain crystallization has been noted in several other monologous series of polymers. Overberger and co-workers, J. Amer. Chem. Soc., 75, 3326 (1953), studies a series of poly(para-alkyl styrenes) with the normal aliphatic groups ($C_2$–$C_{10}$) substituted in the para position. They found a maximum in the glass transition temperature occurring with the $C_{10}$ side chain. If one adds the length of a four-carbon unit for the approximate size of the para-phenylene moiety, then the total chain length would be similar to a $C_{14}$ carbon chain rather than a $C_{10}$ chain:

No direct evidence (x-ray data, etc.) was obtained for crystallinity in the polymers prepared. This does not rule out the proposed explanation for the variation in properties as function of chain length, since small-size crystallites cannot always be recognized in a polymeric matrix by x-ray analysis techniques. Purity of the monomer feed stock was ruled out as a factor for this variation since a similar trend was found for polymers prepared from highly purified monomers. The permeation data obtained from the ter-polymer systems (Table I) also support this theory of competitive plasticization versus side chain crystallization as a causative factor for the maximum obtained for the physical properties.

TABLE I

| | Permeability of Terpolymers | |
|---|---|---|
| Olefin[a] | $O_2$ transmission cc-mil/ in²-yr-atm | $CO_2$ transmission, cc-mil/ in²-yr-atm |
| 90 Hexene-10 hexadecene | 1,860 | 6,870 |
| 90 Hexene-10 hexadecene (plasticized)[b] | 4,340 | |
| 50 Hexene-50 hexadecene | 9,960 | 49,630 |
| 16.7 Hexene-83.3 hexadecene | 33,070 | 110,250 |
| 3.3 Hexene-96.7 hexadecene | 37,530 | 142,300 |
| 16.7 Hexadecene-83.3 octadecene | 34.730 | 154,700 |
| 50 Hexadecene-50 octadecene | 46,700 | 191,900 |

[a]Figures before olefin indicate concentration in wt-%.
[b]Hexadecene, 10 wt-%, used as a plasticizer for the hexene-sulfur dioxide copolymer.

Many membrane devices have been constructed of silicone rubber materials largely because of their high oxygen and carbon dioxide permeabilities and their reasonable non-thrombogenic properties. However, the poor mechanical properties of pure polysilicone materials require the use of high concentrations of silica filler which compromise their ultimate performance as a blood compatible biomaterial. This invention, as described herein, utilizes a material not to our knowledge previously evaluated for blood oxygenation purposes and which shows better physical properties in the pure state than silicone rubber, and also comparable gas permeability and nonthrombogenic properties relative to silicone rubber.

For example, to illustrate the high biocompatibility towards blood, the classical Lee White clotting time method was used. (R. I. Lee and P. D. White. "A Clinical Study of the Coagulation Time of Blood," Am. J. Med. Sci. 145, 495 (1913).

The following average whole blood clotting times (WBCT) were obtained for borosilicate glass and the $C_{16}$ olefin-based polysulfone:

TABLE II

| Surface | Lee White Clotting Time (min) |
|---|---|
| Glass, borosilicate | 8.0 |
| Polysulfone coated pyrex glass | 27.0 |

A typical literature WBCT value for silicone rubber is 27 minutes (Boretos, J. W., Pierce, W. S. "Segmented Polyurethane: A Polyether Polymer. An Initial Evaluation for Biomedical Applications." J. Biomed. Mater. Res. Vol. 2, p. 12, (1968).

The high biocompatibility of the polysulfones of this invention, as illustrated by the foregoing Lee White test, indicates that this material will have utility for the fabrication of prosthetic devices in contact with body fluids, for example, heart valves, surgical implants, artificial arteries and veins, soft contact lenses, and drug delivery systems.

In addition the high biocompatibility coupled with high permeability suggests their utility for surgical tape and wound dressings.

The inate flexibility and ease of forming, both by solvent casting and thermoplastic extrusion, coupled with the high biocompatibility suggests their use for surgical tubing as for example in blood transfusion, intravenous feedings, etc.

To indicate the utility of permeable membranes as blood oxygenators, a man at rest consumes approximately 18 liters per hour of oxygen. Therefore about two square yards of the $C_{16}$ based polysulfone polymer fabricated into a well designed perfusion device would be adequate for life support.

The high permeability of the polysulfone polymers coupled with their potential low cost makes them commercially interesting. These polymers have excellent flexibility, fair transparency and solvent castability. It can be extruded and heat-sealed.

Permselective membranes have also been used for:
instrumentation for gas analysis;
separation, purification and enrichment of gases;
preventing passage of micro-organisms in the pharmaceutical and fermentation industries. Also for surgical dressings and breathing systems in general.

BRIEF DESCRIPTION OF THE DRAWINGS

The physical properties of the copolymers are illustrated in FIGS. 1 through 5, FIG. 1 showing a plot of the alpha-olefin chain length (containing from $C_6$ to $C_{18}$ carbon atoms) against the melt temperature.

The use of the alpha-olefin/$SO_2$ copolymer is illustrated in FIG. 6 which shows a soft contact lens article 5 made from the readily processable copolymer of the alpha-olefin and $SO_2$.

Figure 7:
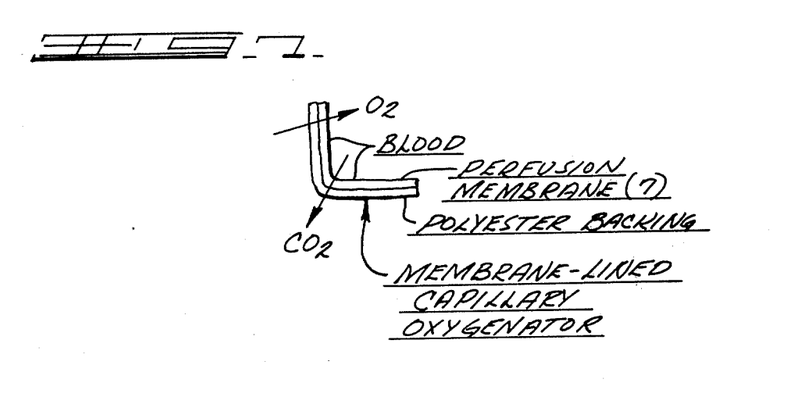
FIG. 7 shows the perfusion membrane 7 of the present invention made from the alpha-olefin/$SO_2$ copolymer.

The membrane 7 is supported by a polyester backing and is used, for instance, in a membrane-lined, capillary oxygenator. As seen in FIG. 7, the membrane 7, made of the alpha-olefin/$SO_2$ copolymer, is in contact with blood. The arrows show $O_2$ entering the blood supply while $CO_2$ leaves the blood through the membrane and the porous polyester backing which, in turn, is supported on porous substrate such as shown, for example, in the membrane-lined capillary oxygenator shown on page 139 of Transactions, American Society for Artificial Internal Organs, 1969.

The copolymers of alpha-olefin and $SO_2$ can be used in many of the biocompatible articles used in contact with body fluids such as artificial arteries, artificial veins, heart valves, surgical implants, blood storage bags and surgical tubing, illustrated in the above article, for example, on pages 170, 173, 179, 201, 212, 207, 246, 251, 256, 287 and 352.

Figure 8:
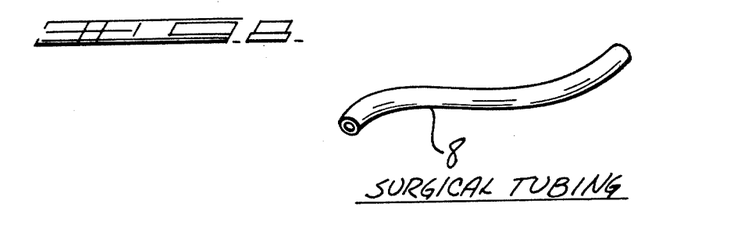

FIG. 8 shows a biocompatible article 8 for contact with human body fluids made of a copolymer of an alpha-olefin and sulfur dioxide, the article being surgical tubing.

Figure 9:
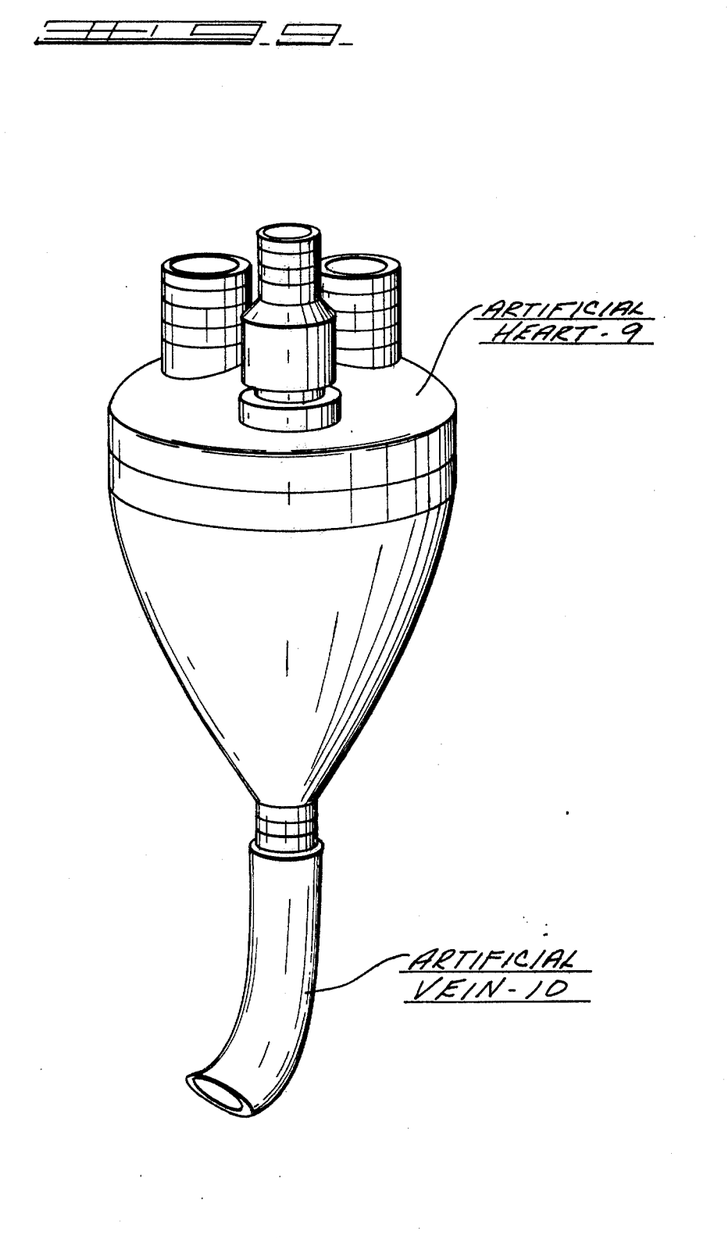
Figure 10:
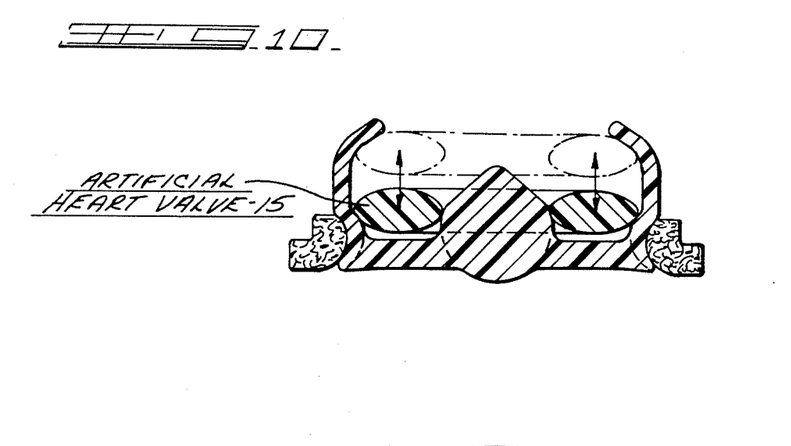
Figure 11:
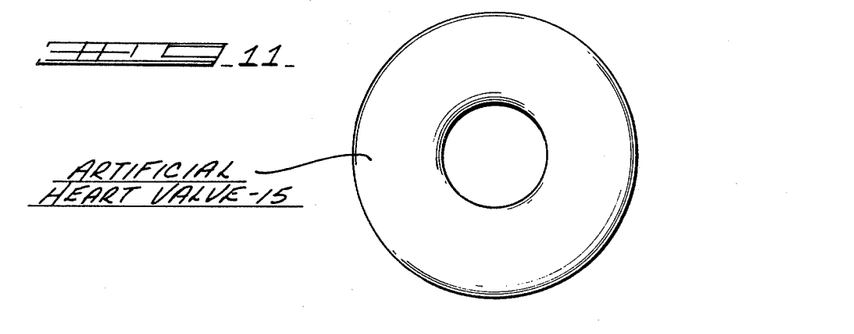

FIG. 9 illustrates a biocompatible article for contact with human body fluids, the article being an artificial heart 9, and an artificial vein 10 connected to the heart. As indicated previously, the biocompatible copolymer of alpha-olefin and sulfur dioxide can be used as an artificial heart valve, which is shown as valve 15 in FIG. 10. The valve 15 is toroidal in shape, and a perspective view of the toroidal valve 15 is shown in FIG. 11.

Figure 12:
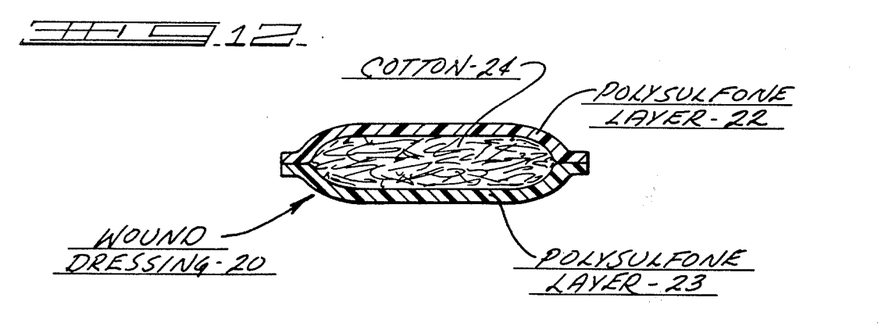

FIG. 12 illustrates another biocompatible article for use in contact with body fluids, the article being a wound dressing 20. The wound dressing 20 comprises a pair of porous polysulfone (copolymer of an alpha-olefin and $SO_2$) layers 22 and 23 with cotton between the two layers. As also shown in FIG. 12, the ends of the polysulfone layers are sealed to provide an excellent dressing.

As previously indicated, outstanding results have been obtained by the use of the alpha-olefin/$SO_2$ copolymers described herein, including the new use of the biocompatible polymer comprising the steps of (1) making a biocompatible article for contact with human body fluids, the article being made of a copolymer of (a) an alpha-olefin having 8 to 18 carbon atoms and (b) sulfur dioxide, and (2) contacting human body fluids with the article of step 1 to provide a nonthrombogenic article having good oxygen and carbon dioxide permeabilities.

What is claimed is:

1. The new use of a polysulfone polymer, the new use comprising the steps of:
   (1) making an article adapted for biomedical surgical implantations of a highly-processable copolymer that is the reaction product of:
      (a) an alpha-olefin having about 16 to 18 carbon atoms; and
      (b) sulfur dioxide; and
   (2) implanting the article of step (1) in a human body as a surgical implant,
   said implanted article characterized by its biocompatibility with human blood.

2. The new use of a polysulfone polymer, the new use comprising the steps of:
   (1) making a permselective membrane article adapted for biomedical usage with human blood of a copolymer of:
      (a) an alpha-olefin having 16 to 18 carbon atoms; and
      (b) sulfur dioxide; and
   (2) oxygenating human blood using the membrane article of step (1),
   said membrane article characterized by its biocompatibility with human blood and its high permeability.

3. The new use of a polysulfone polymer, the new use comprising the steps of:
   (1) making a permselective membrane article adapted for biomedical usage of a copolymer of:
      (a) an alpha-olefin having 16 to 18 carbon atoms; and
      (b) sulfur dioxide; and
   (2) separating components of gases in biomedical procedures using the permselective membrane of step (1), said permselective membrane article characterized by its biocompatibility with human blood.

4. The new use of a polysulfone polymer, the new use comprising the steps of:
   (1) making a prosthetic article adapted for biomedical usage of a copolymer of:
      (a) an alpha-olefin having 16 to 18 carbon atoms and
      (b) sulfur dioxide; and
   (2) using the prosthetic article of step (1) as biomedical surgical tubing to transport blood to and from a human body,
   said prosthetic article characterized by its biocompatibility with said blood.

5. The new use of a polysulfone polymer, the new use comprising the steps of:
   (1) making a biomedical article adapted for contact with human blood, the article being made of a copolymer of
      (a) an alpha-olefin having 16 to 18 carbon atoms and
      (b) sulfur dioxide; and
   (2) contacting human blood with the article of step (1), said article characterized by its biocompatibility and nonthrombogenic properties and its good oxygen and carbon dioxide permeabilities.

6. An article of manufacture for use in contact with human blood and characterized by its biocompatibility therewith, surgical tubing formed of a polysulfone copolymer that is a reaction product of:
   A. An alpha-olefin having 16 to 18 carbon atoms, and
   B. sulfur dioxide.

7. An article of manufacture, a wound dressing for use in contact with the human body and in contact with human blood and characterized by its biocompatibility therewith, said article made of polysulfone copolymer that is a reaction product of:
(1) an alpha-olefin having 16 to 18 carbon atoms, and
(2) sulfur dioxide,
said copolymer having an oxygen transmission rate of about 1 to $4 \times 10^{-4}$ CC MIL/IN$^2$ YR. ATM.

8. An article of manufacture, an artificial artery for use biomedically with the human body and in contact with human blood and characterized by its biocompatibility therewith, said article made of a polysulfone copolymer that is a reaction product of:
(1) an alpha-olefin having 16 to 18 carbon atoms, and
(2) sulfur dioxide,
said artificial artery having a combination of additional properties making it useful in biomedical applications including good tensile strength, good elongation, and non-thrombogenicity.

9. An article of manufacture, an artificial vein for use biomedically with the human body and in contact with human blood and characterized by its biocompatibility therewith, said article made of a polysulfone copolymer that is a reaction product of:
(1) an alpha-olefin having 16 to 18 carbon atoms, and
(2) sulfur dioxide,
said vein having a combination of additional properties making it useful in biomedical applications, including good tensile strength, good elongation, and non-thrombogenicity.

10. An article of manufacture, a heart valve for use biomedically with the human heart and in contact with human blood and characterized by its biocompatibility therewith, said article made of a copolymer that is a reaction product of:
(1) an alpha-olefin having 16 to 18 carbon atoms and
(2) sulfur dioxide,
said heart valve having a combination of additional properties making it useful in biomedical applications, including good tensile strength, good elongation, and non-thrombogenicity.

11. An article of manufacture, a surgical implant for use biomedically in the human body and in contact with human blood and characterized by its biocompatibility therewith, said article made of a polysulfone copolymer that is a reaction product of:
(1) an alpha-olefin having 16 to 18 carbon atoms, and
(2) sulfur dioxide,
said surgical implant having a combination of additional properties making it useful in biomedical applications, including good tensile strength and elongation, non-thrombogenicity, oxygen transmission rate of about 1 to $4 \times 10^{-4}$ CC MIL./IN$^2$ YR ATM. and a $CO_2$ transmission rate of about 4 to $17 \times 10^{-4}$ CC MIL./IN$^2$ YR ATM.

* * * * *